United States Patent [19]
Prater

[11] B 3,987,070
[45] Oct. 19, 1976

[54] PROCESS FOR THE PRODUCTION OF LOW MOLECULAR WEIGHT CYCLOALIPHATIC DIGLYCIDYL ESTERS

[75] Inventor: Klaus Prater, Krefeld-Bockum, Germany

[73] Assignee: Bayer Aktiengesellschaft, Germany

[22] Filed: Feb. 3, 1975

[21] Appl. No.: 546,295

[44] Published under the second Trial Voluntary Protest Program on January 20, 1976 as document No. B 546,295.

[30] Foreign Application Priority Data
Feb. 8, 1974 Germany............................ 2405933

[52] U.S. Cl. ............................................. 260/348.6

[51] Int. Cl.$^2$....................................... C07D 301/30
[58] Field of Search .................................. 260/348.6

*Primary Examiner*—Norma S. Milestone
*Attorney, Agent, or Firm*—Connolly and Hutz

[57] ABSTRACT

Colorless low-viscosity diglycidyl esters of cycloaliphatic dicarboxylic acids of low molecular weight and with a high epoxide group content are obtained in substantially quantitative yields by reacting the cycloaliphatic dicarboxylic acids with excess epihalohydrin in the presence of 0.5 to 4 % by weight based on the dicarboxylic acid of secondary and/or tertiary O-alkali phosphate as catalyst at 80° to 115°C, followed by dehydrohalogenation of the 3-halogen-2-hydroxy propyl carboxylic acid esters formed with aqueous alkali.

1 Claim, No Drawings

PROCESS FOR THE PRODUCTION OF LOW MOLECULAR WEIGHT CYCLOALIPHATIC DIGLYCIDYL ESTERS

This invention relates to a process for the production of low molecular weight, colourless, low viscosity, cycloaliphatic diglycidyl esters.

It is known that 2,3-epoxy propyl carboxylic acid esters can be obtained by reacting the alkali salts of monocarboxylic and polycarboxylic acids with epihalohydrins in the presence of water, quaternary ammonium salts or other catalysts as reaction accelerators. Working this process on an industrial scale involves fairly rigorous reaction conditions, such as the application of pressure and elevated temperatures. In addition, the alkali halide which accumulates in very finely dispersed form during this reaction gives rise to difficulties when it comes to working up (cf. Belgian Pat. No. 588,009, page 2). The epoxide oxygen content is far below the theoretically obtainable values. The residual halogen contents amount to several percent, which complicates their use in the electrical insulation field, because products of this kind show a tendency to evolve hydrogen halides at elevated temperatures, even in hardened form. Efforts to produce the 2,3-epoxy propyl esters from glycide and carboxylic acid chlorides produced unsatisfactory results as well (cf. German Auslegeschrift No. 1,033,204).

It is also known that 2,3-epoxy propyl carboxylic acid esters can be obtained by reacting carboxylic acids with epihalohydrins at elevated temperature in the presence of a tertiary amine or a quaternary ammonium salt. This reaction yields a mixture of 3-halogen-2-hydroxy propyl carboxylic acid esters or the isomeric 3-hydroxy-2-chloropropyl carboxylic acid esters and 2,3-epoxy propyl carboxylic acid esters which actually show a tendency towards polymerisation or gelation when the epihalohydrin is distilled off under the catalytic effect of the nitrogen bases added, and have much lower epoxide contents than are theoretically obtainable (cf. German Auslegeschriften No. 1,033,204 and No. 1,165,030, columns 6 and 7). It has also been found that tertiary amines or quaternary ammonium salts of this kind also have a polymerising effect on epichlorhydrin alone (cf. Journal of Organic Chemistry, 26, page 2681 (1961); German Auslegeschrift No. 1,165,030, column 6).

It is also known from German Auslegeschrift No. 1,165,030 that the reaction of polycarboxylic acids with epihalohydrins can be carried out in the presence of high molecular weight ion exchangers or polyamides which are insoluble in the reaction mixture. Large quantities of catalysts and, preferably, from 10 to 40 mols of epihalohydrin per carboxyl group and, in addition, 3% of water as co-catalyst are used for this purpose. The products obtained by this process contain, in addition to 50 to 60% of the theoretical epoxide group content, relatively large quantities of chlorine which can only be removed by a further treatment with catalyst and fresh epichlorhydrin. However, a repetition of the test showed that this residual chlorine is only partly removed by this treatment.

Finally, it is known from German Pat. No. 1,211,177 that 2,3-epoxy propyl esters (glycidyl esters) of cycloaliphatic monocarboxylic and polycarboxylic acids can be obtained by heating the cycloaliphatic carboxylic acids for prolonged periods at temperatures in the range from 30° to 90°C in the presence of excess epichlorhydrin and in the presence of low molecular weight thioethers or sulphonium salts, and converting the resulting 3-chloro-2-hydroxy propyl esters into the glycidyl esters by treatment with agents liberating hydrogen chloride. The disadvantage of this process is that the reaction times required to from the 3-chloro-2-hydroxy propyl ester are too long, in addition to which the end product is yellow in colour. Moreover the end product has an odour reminiscent of mercaptan.

The object of the present invention is to provide an improved process for the production of glycidyl esters of cycloaliphatic dicarboxylic acids which process does not have any of the disadvantages referred to previously. In other words, the glycidyl esters products should be monomeric and low molecular weight in nature; they should have as high an epoxide group content as possible coupled with a low halogen content; and they should be as colourless and have as low a viscosity as possible.

According to the invention, this object is achieved by carrying out the reaction of the cycloaliphatic dicarboxylic acids with epihalohydrin in the presence of secondary or tertiary potassium or sodium salts of orthophosphoric acid.

Dehydrohalogenation is preferably carried out with aqueous alkalis.

Accordingly, the invention relates to a process for the production of low molecular weight, low viscosity diglycidyl esters of cycloaliphatic dicarboxylic acids by reacting the cycloaliphatic dicarboxylic acids with excess epihalohydrin at 80° to 115°C in the presence of a catalyst, and subjecting the 3-halogen-2-hydroxy propyl carboxylic acid esters formed to dehydrohalogenation with aqueous alkali, characterised by the fact that secondary and/or tertiary o-alkali phosphate is used as catalyst in a quantity of from 0.5 to 4% by weight, based on the dicarboxylic acid.

It is preferred to use from 1 to 3% by weight of secondary or tertiary o-alkali phosphate, the preferred alkali phosphate being potassium phosphate.

Suitable cycloaliphatic dicarboxylic acids include cyclohexane dicarboxylic acids, such as hexahydrophthalic acid, methyl hexahydrophthalic acids, hexahydroisophthalic acid, hexahydroterphthalic acid, also the esterification products of 2 mols of cyclohexane dicarboxylic acid anhydride with 1 mol of a mono-, di- or tri-alkylene glycol. It is preferred to use hexahydrophthalic acid, although mixtures of the dicarboxylic acids can also be used.

However, it is readily possible, instead of using the free acids, to use their anhydrides. In this case, the anhydride is dissolved in an excess of epihalohydrin, somewhat more (approximately 0.1 to 0.6 mol %) than the quantity of water required to hydrolyse the anhydride is added and the mixture heated to a temperature in the range from about 70° to 110°C, preferably to a temperature of 90°C. Hydrolysis is complete after 2 to 3 hours. The excess water does not have to be removed. The further reaction takes place in the manner described hereinafter.

Suitable epihalohydrins include epichlorhydrin, epibromhydrin and methyl epichlorhydrin. It is preferred to use epichlorhydrin.

The quantity in which the epihalohydrin is used can be from 2 to 20 mols per mol of carboxyl group. It is preferably used in a quantity of from 4 to 6 mols.

The process according to the invention can be carried out in the manner described hereinafter. The cycloaliphatic dicarboxylic acid is heated with an excess of epihalohydrin to a temperature of from 80° to 115°C, preferably from 85° to 100°C, in the presence of 0.5 to 4% by weight, preferably 1 to 3% by weight, of secondary and/or tertiary o-alkali phosphate, and the reaction mixture is maintained at this temperature until the acid number is 0, in other words following the addition of phenol phthalein, a sample of the mixture (approximately 2 to 4 g) should change to pink in colour after the addition of only 0.1 to 0.2 ml of 0.1 N NaOH. In general, this point is reached after 3 to 4 hours. The entire cycloaliphatic dicarboxylic acid is then present in the form of bis-3-chloro-2-hydroxy propyl ester (bis-halohydrin ester).

The subsequent dehydrohalogenation reaction may be carried out as follows. The reaction product from the first stage is cooled to approximately 20°C. Thereafter approximately 50% aqueous alkali hydroxide, preferably sodium hydroxide, is added with stirring. The quantities of alkali hydroxide should be such that from 1.1 to 1.4 mols, preferably from 1.2 to 1.25 mols, of alkali hydroxide are available per halohydrin ester group. When the alkali is added, the temperature of the mixture should not exceed 30°C. Following addition of the alkali, a gentle vacuum is applied and excess epichlorhydrin (substantially quantitative) and water are distilled off from the reaction mixture. The temperature is gradually increased and the pressure continuously reduced until the sump temperature is 90°C and the pressure is in the range from 10 to 20 mm. The residue is dissolved in a solvent, for example toluene, and washed with water until the aqueous phase has a pH-value in the range from 6 to 7. In order further to reduce the halogen content, the organic phase can be treated again with substantially equivalent quantities of approximately 50% aqueous alkali. Working up yields a low-viscosity, colourless and almost odourless oil with a high epoxide group content. The viscosities at 20°C amount to approximately 500 to 900 cP, the halogen values to from 0.6 to 0.9% by weight and the epoxide equivalents to from 155 to 170.

The surprising technical advance of the process according to the invention over conventional processes is embodied in the fact that, despite the short reaction times at 80° to 115°C, the 3-halogen-2-hydroxy propyl esters of the cycloaliphatic dicarboxylic acids are obtained in substantially quantitative yields without being contaminated by isomeric 3-hydroxy-2-halogen propyl esters and other polymeric halogen-containing products. Thus, low-viscosity diglycidyl esters with a high epoxide group content can be obtained after the subsequent dehydrohalogenation stage. The products according to the invention are substantially crystal-clear, whereas conventional processes yield more or less coloured products. Finally, the products obtained in accordance with the invention are substantially odourless, which is not the case with products produced using thioethers or sulphonium salts as catalysts.

The diglycidyl esters obtained in accordance with the invention may be crosslinked with the usual hardeners, such as cyclic or linear carboxylic acid anhydrides, polycarboxylic acids, aliphatic, aromatic, and/or cycloaliphatic amines and polyamines, $BF_3$-complexes, etc. By virtue of their favourable dielectric properties, the hardened products are of considerable significance, especially in the electrical insulation field. In addition, the diglycidyl esters according to the invention may be used as stabilisers for chlorine-containing compounds and polymers.

EXAMPLE

Hexahydrophthalic acid diglycidyl ester 4163 g of epichlorhydrin, 693 g of hexahydrophthalic acid anhydride and 105 g of distilled water were weighed into a 6-liter four-necked flask, equipped with a reflux condenser, gas inlet pipe and dropping funnel, and heated with stirring to 90°C. A gentle stream of nitrogen was passed over the reaction mixture. After 2.5 hours, 15 g of $K_2HPO_4$ (secondary o-potassium phosphate) were added and the mixture was kept for about another 4 hours at 90°C. Thereafter, the product had an acid number of 0. It was cooled to approximately 20°C, followed by the dropwise addition over a period of 1 to 2 hours of 882 g of 45% by weight of NaOH. The sump temperature should not exceed 30°C during the addition. A water jet vacuum was then applied, and water together with excess epichlorhydrin (substantially quantitative) was distilled off. After the sump temperature had reached 90°C and the vacuum settled at approximately 20 mm, the product was taken up with 1000 g of toluene and washed with water until salt-free.

For further dehydrohalogenation, the product was heated to reflux temperature (118°C) following separation of the aqueous, salt-containing phase, and 80 g of 45% by weight NaOH were slowly added dropwise over a period of 4 hours, during which the water was azeotropically distilled off. After cooling to approximately 20° to 25°C, the product was washed once with 400 g of water and then with 150 g of a concentrated aqueous $NaH_2PO_4$-solution. The solution should have a pH-value of 6 or lower. The toluene is distilled off under normal conditions and the residue blown out with a powerful stream of nitrogen for 3 hours at 120°C in order to remove residues of volatile constituents. After cooling, the product was filtered through a suction filter, giving a low-viscosity, substantially colourless and substantially odourless resin.

Yield: 1160 g ~ 97% of the theoretical yield
Hazen colour index: approximately 20
Epoxide equivalent: 165
Chlorine content: approximately 0.73
Viscosity at 20°C: 689 cP (Hoppler drop-ball viscosimeter).

I claim:

1. A process for the production of low molecular weight, low viscosity diglycidyl esters of cycloaliphatic dicarboxylic acids by reacting the cycloaliphatic dicarboxylic acids with excess epihalohydrin in the presence of a catalyst at 80° to 115°C, followed by dehydrohalogenation of the 3-halogen-2-hydroxy propyl carboxylic acid esters formed with aqueous alkali, wherein secondary and/or tertiary o-alkali phosphate is used as catalyst in a quantity of from 0.5 to 4% by weight, based on the dicarboxylic acid.

* * * * *